(12) United States Patent
Jin et al.

(10) Patent No.: US 8,779,024 B2
(45) Date of Patent: Jul. 15, 2014

(54) ACID-NEUTRALIZING RESINS AND HARDENABLE DENTAL COMPOSITIONS THEREOF

(71) Applicants: Xiaoming Jin, Middletown, DE (US); Huaibing Liu, Dover, DE (US)

(72) Inventors: Xiaoming Jin, Middletown, DE (US); Huaibing Liu, Dover, DE (US)

(73) Assignee: DENTSPLY International Inc., York, PA (US)

( * ) Notice: Subject to any disclaimer, the term of this patent is extended or adjusted under 35 U.S.C. 154(b) by 43 days.

(21) Appl. No.: 13/773,684

(22) Filed: Feb. 22, 2013

(65) Prior Publication Data
US 2013/0225716 A1    Aug. 29, 2013

Related U.S. Application Data

(60) Provisional application No. 61/604,006, filed on Feb. 28, 2012.

(51) Int. Cl.
*C08L 101/02* (2006.01)
*A61K 6/083* (2006.01)
*C08F 297/02* (2006.01)
*A61K 6/00* (2006.01)

(52) U.S. Cl.
CPC ............ *A61K 6/0835* (2013.01); *A61K 6/0023* (2013.01); *A61K 6/0067* (2013.01); *A61K 6/083* (2013.01)

USPC .......................................... 523/115; 525/242

(58) Field of Classification Search
None
See application file for complete search history.

(56) References Cited

U.S. PATENT DOCUMENTS

| 8,552,130 | B2 * | 10/2013 | Lewandowski et al. ....... 526/263 |
| 2006/0063854 | A1 * | 3/2006 | Jin et al. ....................... 523/115 |
| 2008/0182948 | A1 * | 7/2008 | Jin et al. .......................... 526/75 |
| 2009/0247715 | A1 * | 10/2009 | Jin et al. .......................... 526/75 |
| 2010/0240914 | A1 * | 9/2010 | Jin et al. ........................ 549/267 |
| 2012/0108837 | A1 * | 5/2012 | Jin et al. ........................ 558/267 |

FOREIGN PATENT DOCUMENTS

WO    WO 2011146356 A1 * 11/2011

OTHER PUBLICATIONS

Swift, EJ; May, KN. AD Journal of Prosthodontics; 7: 256-60, 1998.
Osada et al; Dental Materials Journal; 21 (11): 1044-50, 2005.

* cited by examiner

*Primary Examiner* — James J Seidleck
*Assistant Examiner* — Peter A Salamon
(74) *Attorney, Agent, or Firm* — Leana Levin; Douglas J. Hura; David Zdurne

(57) ABSTRACT

Disclosed herein are acid-neutralizing polymerizable and/or non-polymerizable resins, methods of making such resins, and dental compositions having such resins.

5 Claims, 13 Drawing Sheets

ACID-NEUTRALIZING RESINS AND HARDENABLE DENTAL COMPOSITIONS THEREOF

TECHNICAL FIELD

Disclosed herein are a class of acid-neutralizing resins and hardenable or curable compositions containing such resins.

BACKGROUND

Chemical polymerization of vinyl or acrylate based resins via a free radical polymerization mechanism at ambient temperature is traditionally achieved using a binary, redox curing system consisting of a peroxide and an aromatic tertiary amine. On the other hand, light-activated polymerization proceeds via the generation of free radicals from the activation of a photoinitiator, usually an α-diketone, to its excited triplet state. This is followed by the reduction of the activated photoinitiator by an amine accelerator to form an intermediate excited complex (exciplex), which releases the free radicals on dissociation. There was evidence to suggest that bond strengths of resin composites to dentin were influenced by the compatibility of the polymerization modes between adhesive systems and resin composites (Swift E J, May K N, Wilder A D. *Journal of Prosthodontics*, 7: 256-60, 1998). A report further revealed that common light-cured, self-etching adhesive systems were incompatible with chemical-cured composites (Miller M B et al. *Realty* 13(1), 182-7, 1999), to the extent that no effective bonding was achieved for some systems. However, the systems that bonded poorly to the chemically cured composites exhibited high shear bond strengths with the use of light-cured resin composites. Generally, the nature of incompatibility of self-etching adhesives with chemical-cured resins is attributed to the in situ reaction between the basic component (amine coinitiatior) of the dual-cure restorative and the acid components of the adhesive system. More specifically, these acid components of the bonding agent are able to readily protonate the tertiary aromatic amine, which could be found in the self-curing resin composite as part of the organic redox catalyst. The protonated amine (quaternary aromatic amine) became inactive and/or not reactive towards the peroxide. Consequently, initiating radicals were able to be generated under ambient conditions. Overall, such a catalyst pair would have a loss in efficiency, and the rate and degree of functional group conversion are significantly diminished compromising the performance of the dental adhesive. In order to avoid such an unwanted amine protonation reaction, the dental restoratives to be used in combination have to be limited to those of the photo-curable type only.

Although light-cured resin composites have largely superseded the use of chemical-cured composites in esthetic dental applications, chemically activated composites still have important applications in contemporary restorative dentistry. The longer working time of chemically cured composites has been adopted in the 'directed shrinkage technique' for posterior resin composite restorations. In this technique, a slow setting, chemically cured composite was used either in bulk or as a basal layer to relieve the stress developed in a restoration by the flow of the partially polymerized material. Chemically cured resins are frequently used as restorative materials in areas that are not easily penetrable by light, and as auto- or dual-curing resin cements for luting of crown and bridges, inlays and onlays along with endodontic posts. In order to facilitate the use of light curing self-etching bonding agents with dual curing or chemically curing composites, a self-curing activator is required to overcome the incompatibility of the acid containing adhesive with the amine in the redox catalyst of the chemically cured system. In the Prime&Bond NT® Dual-Cure bonding system available from DENTSPLY International, Inc., the regular light-cure bonding agent, Prime&Bond NT® is mixed with Self-Cure Activator prior to use. The Prime&Bond NT® Dual-Cure exhibits excellent bond strength when bonding a dual-cure cement, e.g. Calibra® available from DENTSPLY International, Inc., in chemical-cure mode.

The Self-Cure Activator developed specifically for Prime&Bond NT® does not necessarily work as well with other simplified adhesives. More importantly, Self-Cure Activator has to be mixed with a simplified adhesive prior to use, which is an extra step for clinicians. There is a real need to simplify the system. It was thought that cement incorporating a base could neutralize acids in a simplified adhesive to mitigate or eliminate the issue of deactivation of amine in the cement. As a result, the incompatibility of a simplified adhesive and resin cement in self-cure mode may be reduced or eliminated.

Osada et al (*Dental materials Journal*, 21(11): 1044-50, 2005) reported that addition of an anion exchange resin to the amine component of self-cured resin was an effective means of enhancing the bond strength on dentin and to prevent amine neutralization through the acid groups of self-etching primer adhesives. The drawback with this approach is that flexural modulus of cement with anion exchange resin drops off. More critically, anion exchange resin is polymerized beads with diameter 1-2 mm, which would result in cement with film thickness too large for any clinical usage.

SUMMARY

Disclosed herein is a method of making an acid-neutralizing resins, a resin composition having an acid-neutralizing capability and polymerizable or hardenable dental compositions for application in dental restorations. More specifically this disclosure is related to a method to prepare such reactive resins containing proper moieties that are capable effectively neutralizing stronger acids to prevent the amine co-initiator existing in any formulated dental restoratives from similar neutralizing reaction. Furthermore such acid-neutralizing resins can be either polymerizable or nonpolymerizable, and it can be further formulated in a variety of hardenable dental compositions, including but not limited to dental adhesives, dual-cure dental cements and dental composites. Thus in this disclosure is a method of effectively neutralizing any residual acid either from cured dental primer or from dental adhesives by dental compositions containing acid-neutralizing polymerizable resin, and consequently sound bonding of dental restoratives to tooth substitutes is readily achieved.

Representative formulas of such base resins may be as follows:

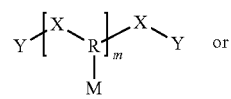

I

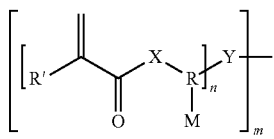

II

R': H or Me;
X: O, S, NH, NR1 (R1=CH3, C2H5)
R and Y: independently of each other, have C1-C24, linear and/or branched alkylene residue, or aromatic/substituted residue;
M: alpha-substituted tertiary amine, pyridine or substituted pyridine, imidazole and/or substituted imidazole, pyrrole and/or substituted parrole, piperidine and/or substituted piperidine, pyrazole and/or substituted pyrazole, oxazole and/or substituted oxazole, thiazole and/or substituted thiozole, isoxazole and/or substituted isoxazole, isothiazole and/or substituted isoxazole, thiadizole indole and/or substituted thiadizole indole, indolizine and/or substituted indolizine, triazole and/or substituted triazole, tetrazole and/or substituted tetrazole, pentazole and/or substituted pentazole, quinoline and/or substituted quinoline, isoquinoline and/or substituted isoquinoline isoquinoline, pyridazine and/or substituted pyridazine, pyrimidine and/or substituted, pyzazine and/or substituted pyzazine, cinnoline and/or substituted cinnoline, phthalzine pyrimidine and/or substituted phthalzine, quinazoline and/or substituted quinazoline, quinoxaline and/or substituted quinoxaline, phenazine and/or substituted triazines, triazines and/or substituted triazines or any combination of these
n=1-10 and m=1-10

This disclosure relates to resin compositions of acid-neutralizing resins and further hardenable or curable compositions containing the said resins. The hardenable or curable compositions are preferably dental compositions, included but not limited to adhesives, cements and composites. This disclosure relates particularly to a method of effectively neutralizing the excess acids in any cured primers, self-etching adhesives or any other adhesive systems so as to allow subsequently adequate curing for good bonding between such adhesive systems and the dual-cure restoratives. Disclosed herein are compositions of such acid-neutralizing resins and the method to utilize such acid-neutralizing resins in formulated compositions that become capable of effectively neutralizing any residual acid and at the same time effectively preventing the similar neutralizing reaction from the amine coinitiators that existed in standard dual-cure restoratives. Thus a significant enhancement in term of hardening or curing process, especially at the interface between the acidic surface and restorative materials should be readily achieved, which consequently results in improved compatibility and more specifically improved bonding strength.

DETAILED DESCRIPTION

In this disclosure, identified are a class of novel additive, acid-neutralizing resins, which could be readily formulated in conventional restoratives and make them capable of neutralizing the acidic component from adhesive and consequently lead to pronounced enhancement in bonding strength due to improved polymerization of the restorative. In addition, as a natural extension of this disclosure, a self-neutralizable adhesive composition should be also formulated by incorporating such polymerizable base resins, which will work similarly towards self-etching primer and any other conventional, dual-cure, self-cure and/or light-cure restoratives. Pronounced improvement in bonding strength was true benefit from such simplified procedures due to incorporation of such polymerizable base resins.

The following formula illustrates the representative structure of such acid-neutralizing resins. It is expected further alteration from such formulate is possible based on basic knowledge in organic chemistry, which should fall in the scope of this disclosure.

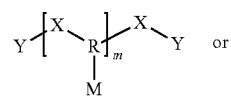

I

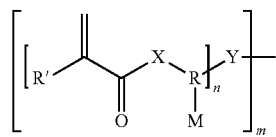

II

R': H or Me;
X: O, S, NH, NR1 (R1=CH3, C2H5)
R and Y: independently of each other, have C1-C24, linear and/or branched alkylene residue, or aromatic/substituted residue;
M: alpha-substituted tertiary amine, pyridine or substituted pyridine, imidazole and/or substituted imidazole, pyrrole and/or substituted parrole, piperidine and/or substituted piperidine, pyrazole and/or substituted pyrazole, oxazole and/or substituted oxazole, thiazole and/or substituted thiozole, isoxazole and/or substituted isoxazole, isothiazole and/or substituted isoxazole, thiadizole indole and/or substituted thiadizole indole, indolizine and/or substituted indolizine, triazole and/or substituted triazole, tetrazole and/or substituted tetrazole, pentazole and/or substituted pentazole, quinoline and/or substituted quinoline, isoquinoline and/or substituted isoquinoline isoquinoline, pyridazine and/or substituted pyridazine, pyrimidine and/or substituted, pyzazine and/or substituted pyzazine, cinnoline and/or substituted cinnoline, phthalzine pyrimidine and/or substituted phthalzine, quinazoline and/or substituted quinazoline, quinoxaline and/or substituted quinoxaline, phenazine and/or substituted triazines, triazines and/or substituted triazines or any combination of these residues;

n=1-10 and m=1-10.

In the following chart, the typical M is illustrated:

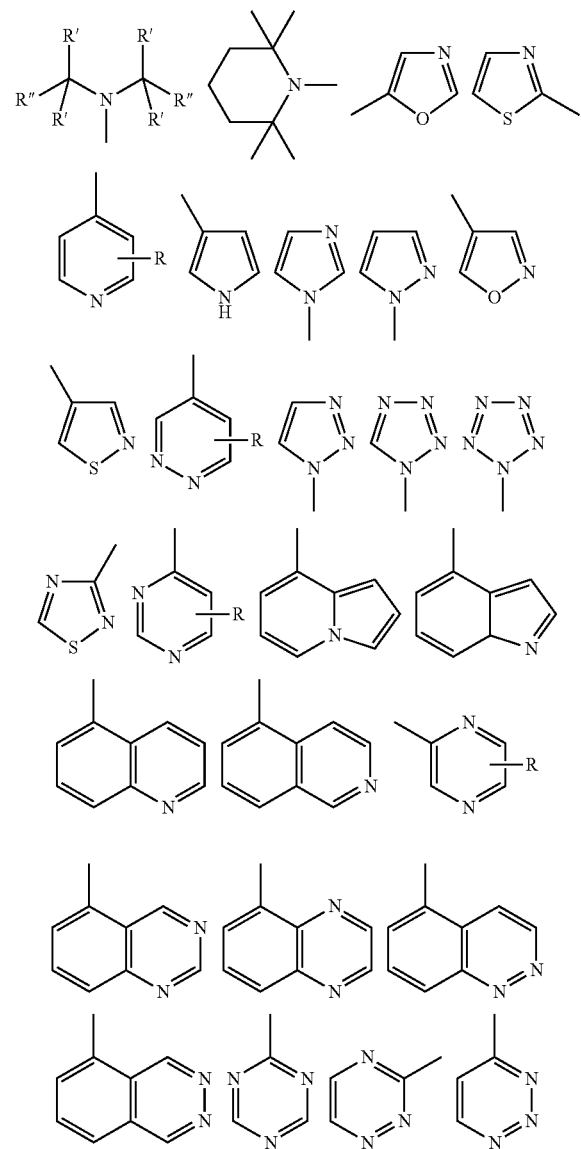

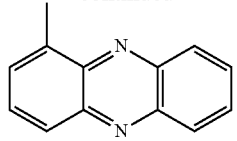

-continued

EXAMPLES

Example 1

Figure 1:
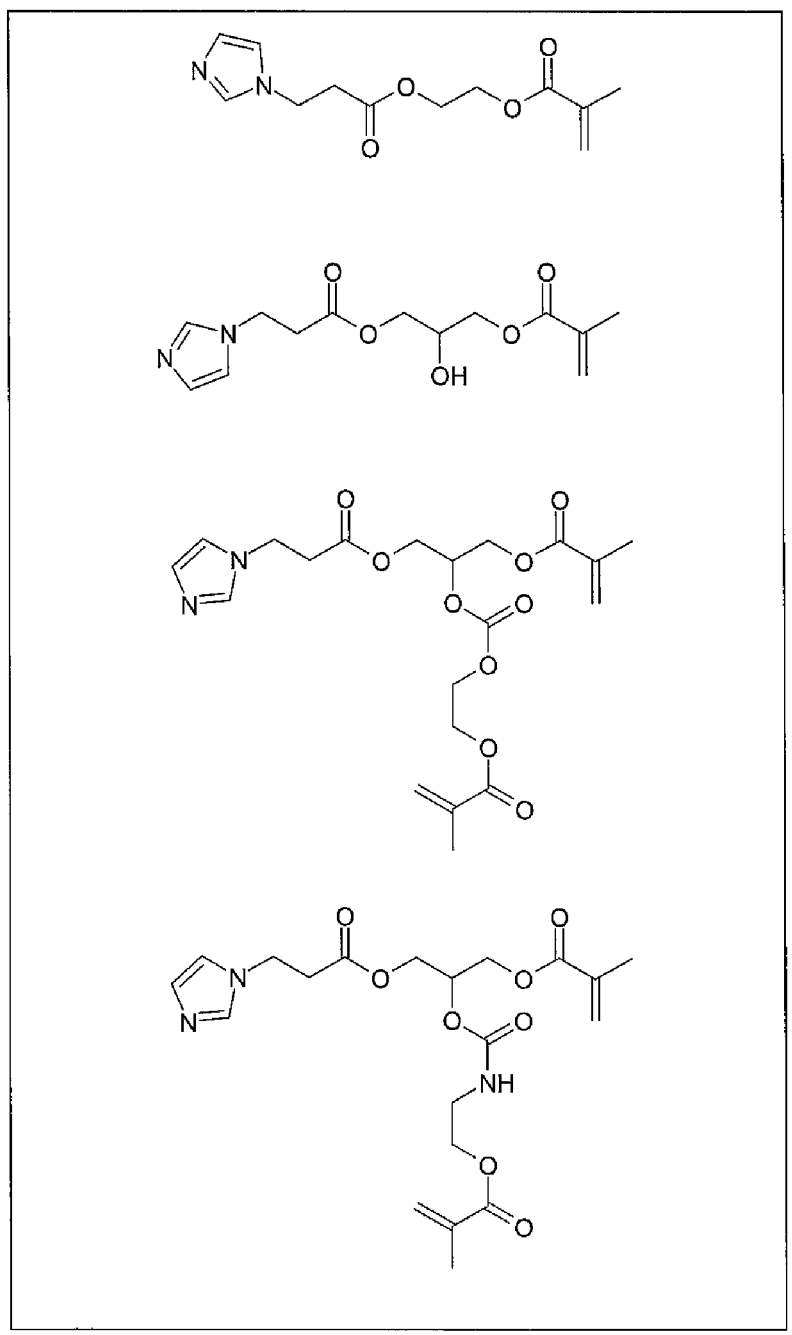
FIG. 1 depicts examples of acid neutralizing polymerizable resins.
Figure 2:
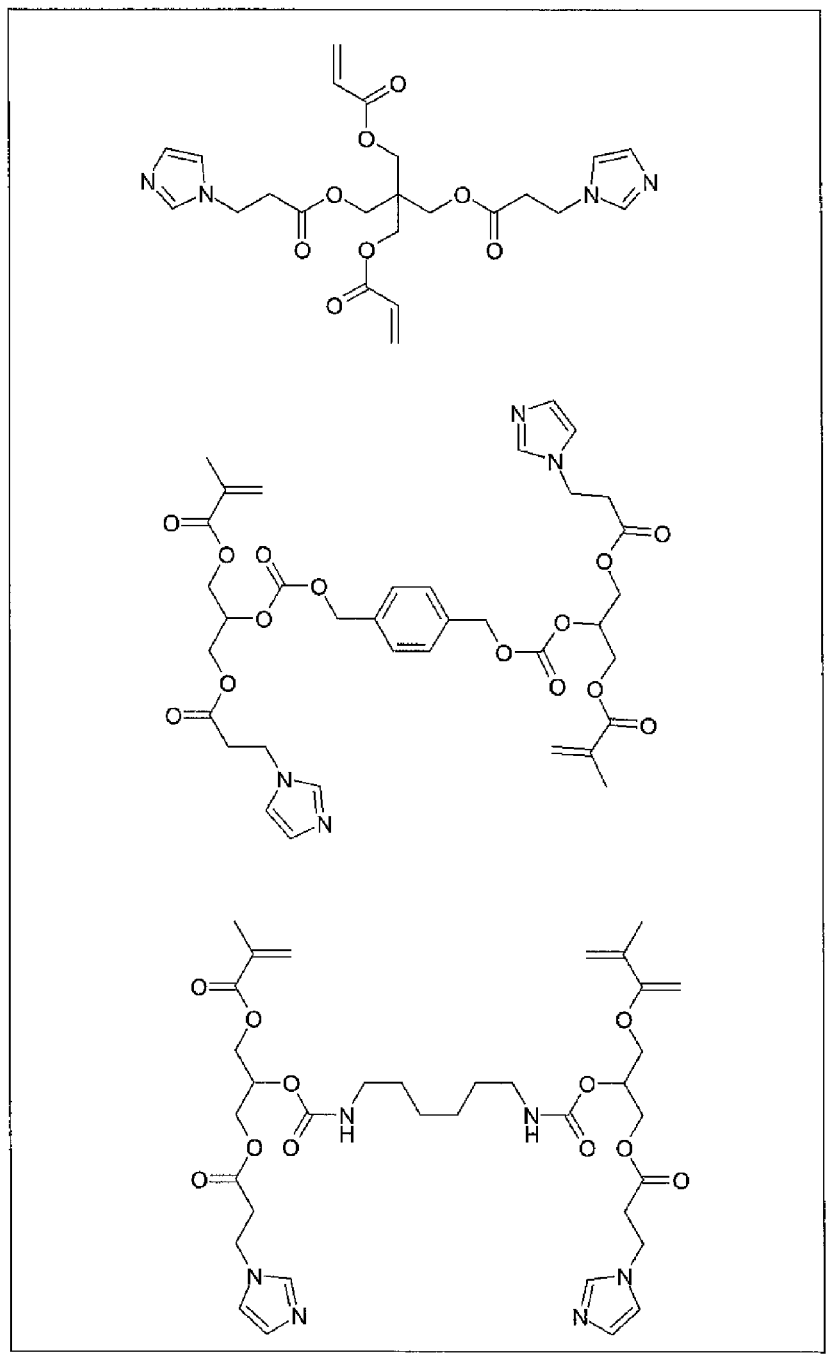
FIG. 2 depicts more examples of acid neutralizing polymerizable resins.
Figure 3:
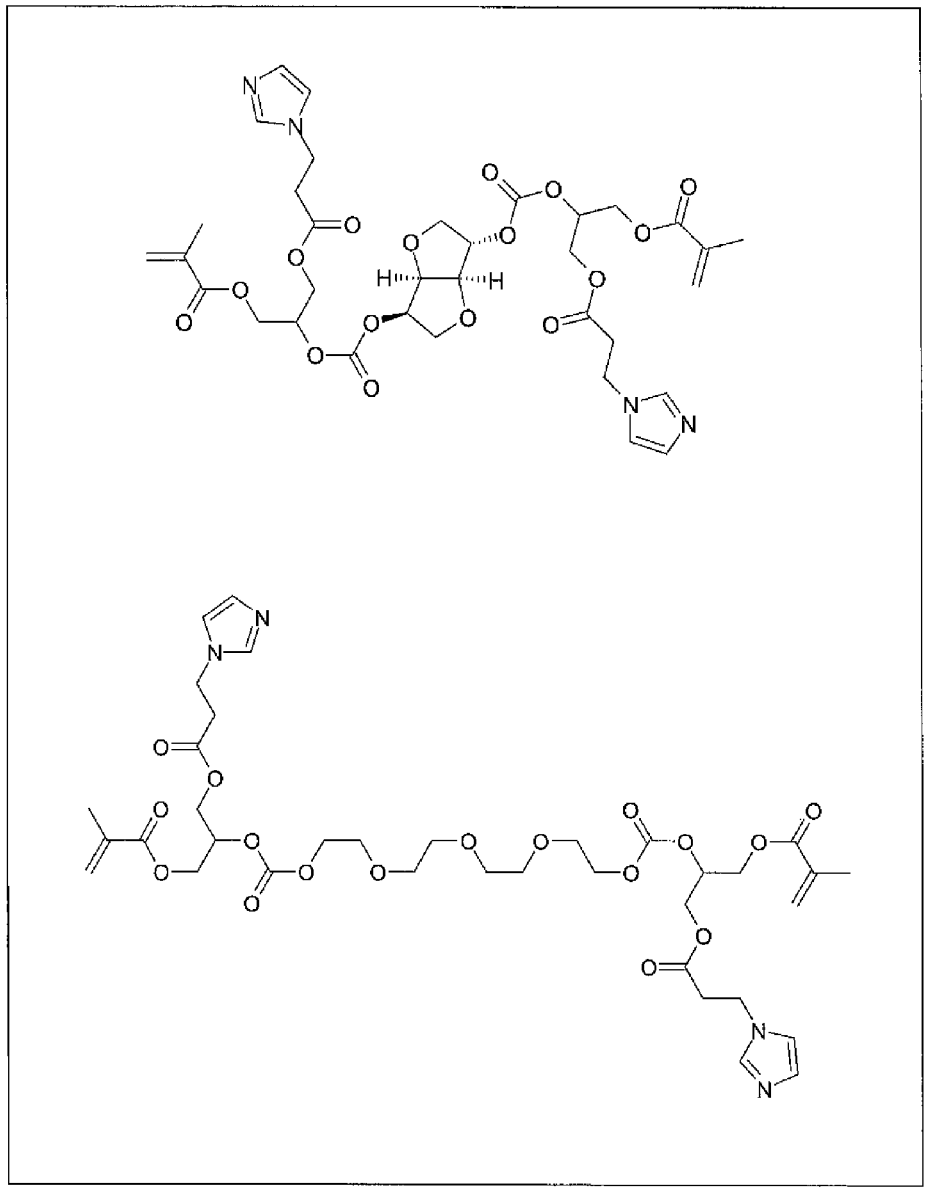
FIG. 3 depicts yet more examples of acid neutralizing polymerizable resins.
Figure 4:
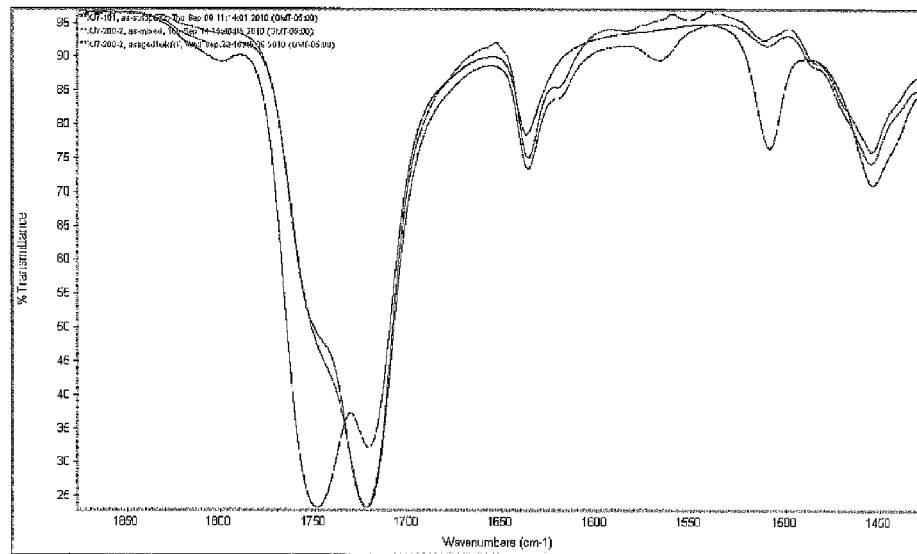
FIG. 4 is a FTIR spectra of a complex of PENTA/bisimidazole dimethacrylate.
Figure 5:
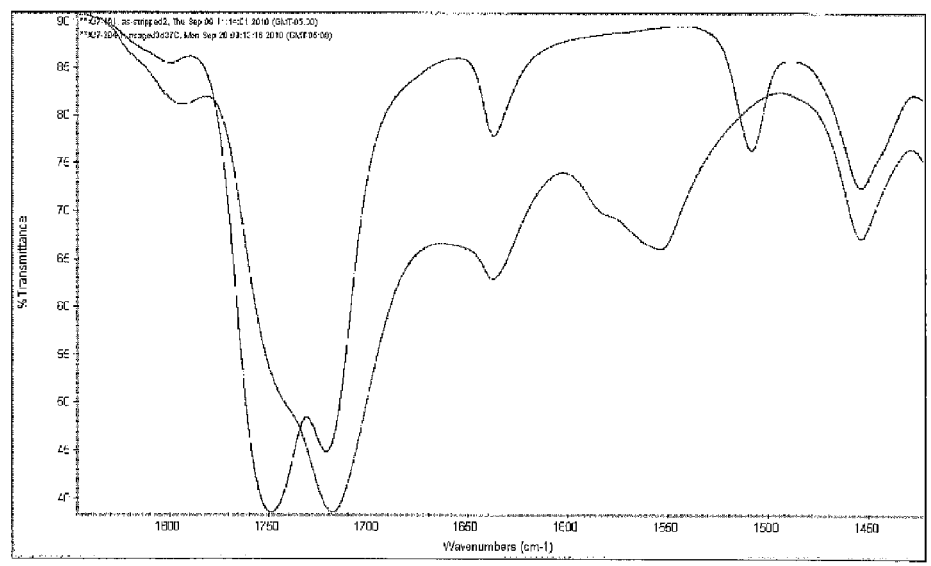
FIG. 5 is a FTIR spectra of a complex of polyacrylic acid/bisimidazole dimethacrylate.
Figure 6:
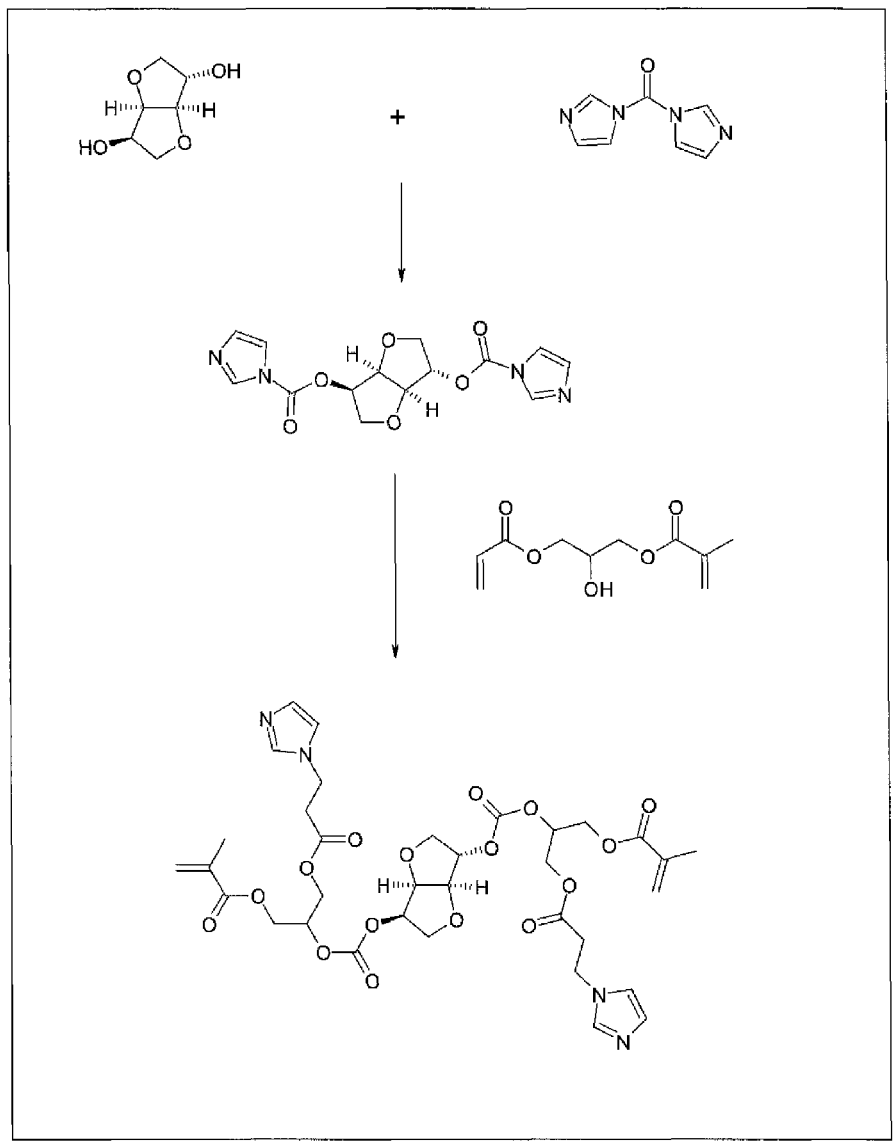
FIG. 6 demonstrates one preparation of isosorbide passed polymerizable imidazole resin.

Isosorbide-based bisimidazoledimethacrylate Resin (FIG. 6) was prepared via a two-step process as described in the following: to a 1000 ml 3-nech round flask, 98.88 g of 1,1-carbonydiimidazole (CDI), 550 g of methylene dichloride and 43.9 g of isosorbide were charged and soon the system turns clear at room temperature. Then the crystal was developed as resulted of imidazole formation. After 2 hrs reaction at RT, 131.1 g of 3-(acryloyloxy)-2-hydroxypropyl methacrylate (AMAHP), 40.0 g of potassium carbonate and 4.0 g of terabutylamoniumbromide were added. Keep the reaction proceeding at room temperature for additional 10-12 hrs prior to 200 ml of water was added to stop the reaction. The resulting solution was extraction several times with water to remove all of imidazole and catalysts. Then it was dried over magnesium sulfate overnight at RT prior to it was filtrated. Solvent was removed via Rotovapor at 35-40° C. under vacuum. 240 g of liquid resin was collected with yield of 89%.

Example 2

Figure 7:
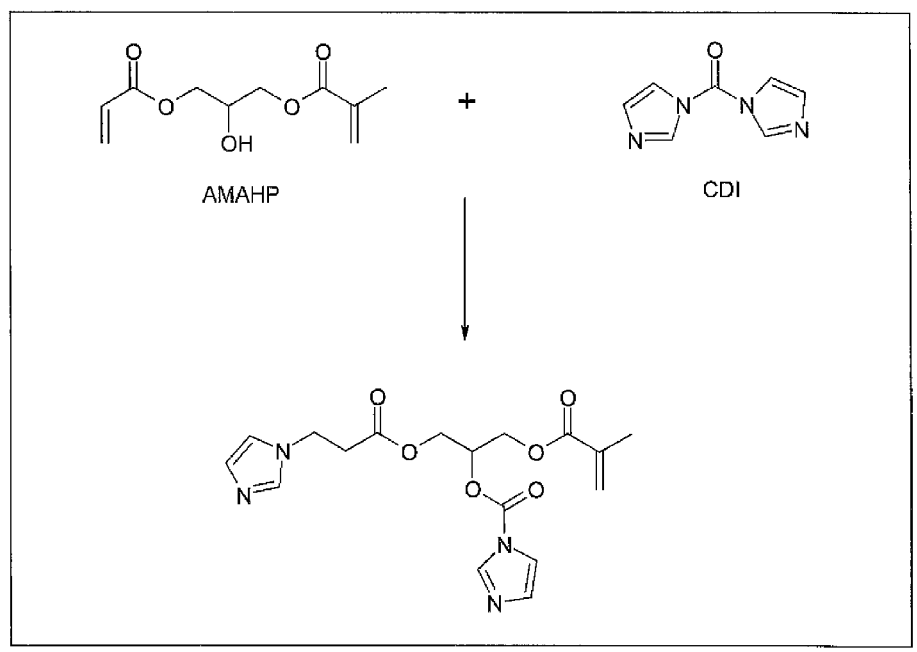
FIG. 7 demonstrates one preparation of AMAHP-based polymerizable imidazole resin via CDI process.
Figure 8:
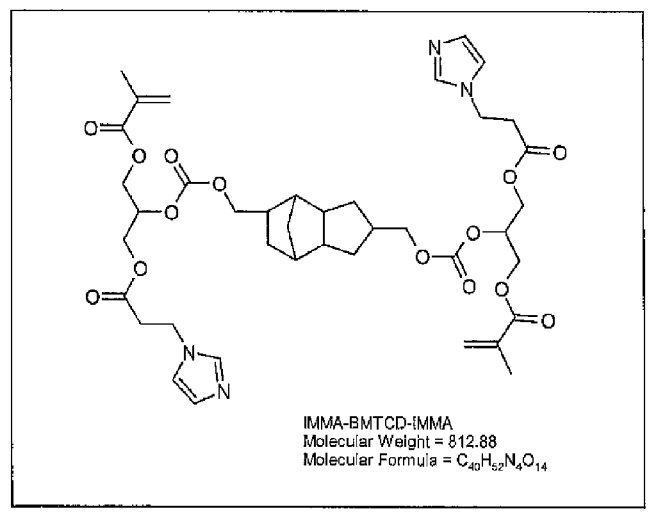
FIG. 8 depicts a TCDC-based bisimidazole dimethacrylate resin.

TCDC-based bisimidazole-dimethacrylate Resins (FIG. 8) was prepared via a two-step process as described in the following: to a 1000 ml 3-nech round flask, 74.45 g of CDI, 400 ml of methylene dichloride and 98.36 g of AMAHP were charged and soon the system turns clear at room temperature. After 6 hrs reaction at RT, a bisimidazole precursor was formed as shown in FIG. 7, then 45.0 g of 4,8-bis(hydroxymethyl)-tricyclo[5,2,1,0$^{2.5}$](TCDC) and 40.0 g of potassium carbonate and 3.8 g of terabutylamoniumbromide were added. Keep the reaction proceeding at room temperature for additional 10-12 hrs prior to 250 ml of DI water was added to stop the reaction. The resulting solution was extraction several times with water to remove all of imidazole and catalysts. Then it was dried over magnesium sulfate overnight at RT prior to it was filtrated. Solvent was removed via Rotovapor at 35-40° C. under vacuum.

Example 3

HEMA-based Monoimidazole-dimethacrylate Resins (FIG. 9) was also prepared via a two-step process as described in the following: to a 1000 ml 3-nech round flask, 81.8 g of CDI, 450 ml of methylene dichloride and 107.5 g of AMAHP were charged and soon the system turns clear at room temperature. After 6 hrs reaction at RT, 66.5 g of HEMA, 40.0 g of potassium carbonate and 4.0 g of terabutylamoniumbromide were added. Keep the reaction proceeding at room temperature for additional 10-12 hrs prior to 200 ml of water was added to stop the reaction. The resulting solution was extraction several times with DI water to remove all of imidazole and catalysts. Then it was dried over magnesium sulfate overnight at RT prior to it was filtrated. Solvent was removed via Rotovapor at 35-40° C. under vacuum.

Example 4

Figure 10:
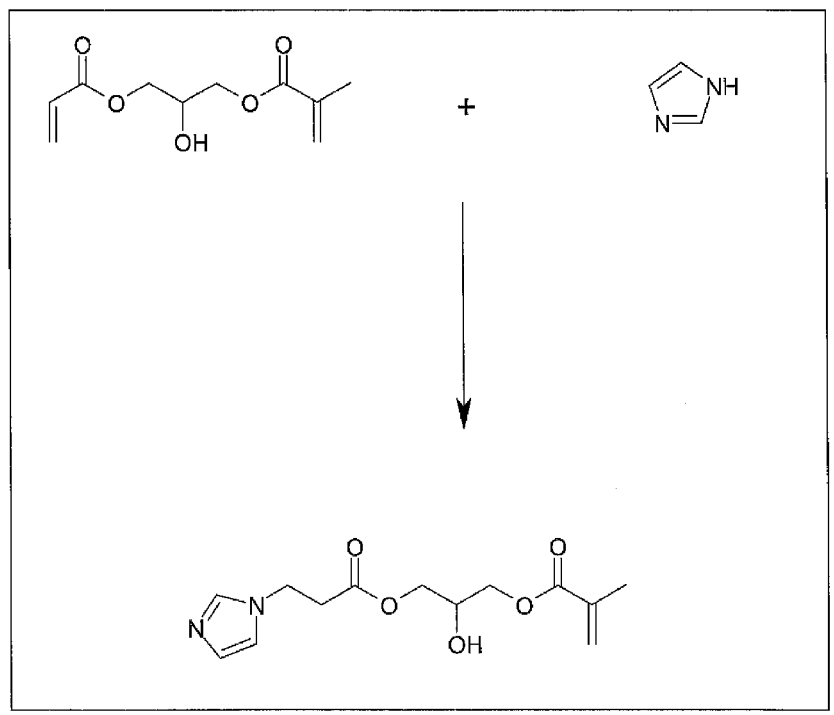
FIG. 10 demonstrates one preparation of AMAHP based polymerizable imidazole resins via an imidazole process.

AMAHP-based monoimidazole-monomethacrylate Resins (FIG. 10) was also prepared via a one-step process as described in the following: to a 1000 ml 3-nech round flask, 102 grams of imidazole, 700 ml of methylene dichloride and 161 grams of AMAHP were charged and soon the system turns clear at room temperature. After reaction over night at RT, the resulting solution was extracted several times by using aqueous solution of potassium carbonate. Then it was dried over night with magnesium sulphate prior to remove the solvent via Rotovapor at 35-40° C. under vacuum. Liquid resin was collected.

Example 5

Figure 11:
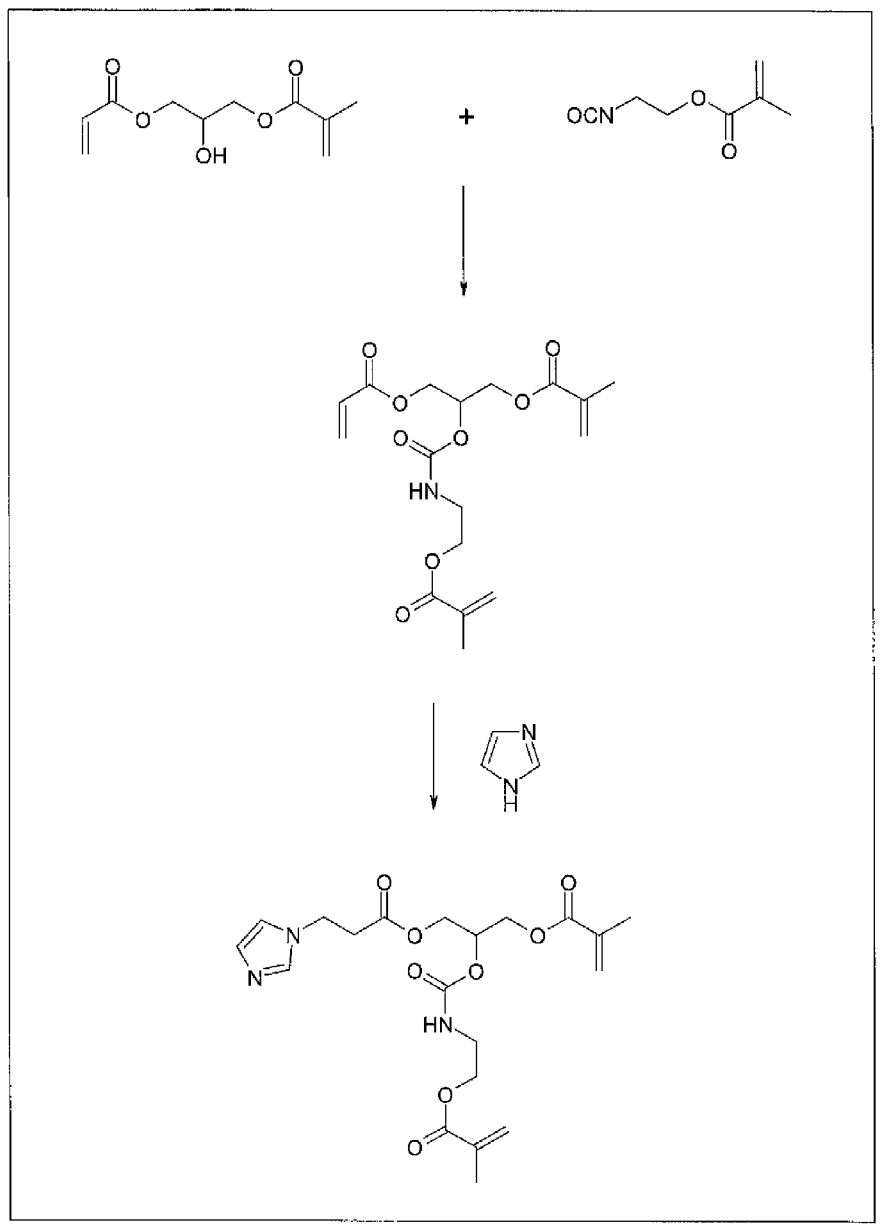
FIG. 11 demonstrates one preparation of an IEM based dimethacrylate imidazole resin.
Figure 12:
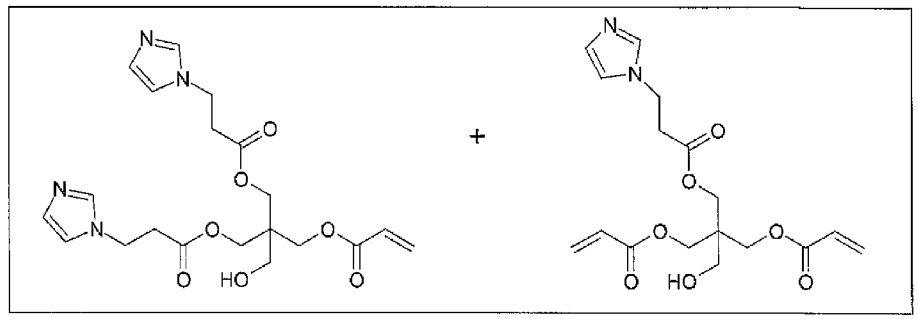
FIG. 12 depicts imidazole acrylate resins.
Figure 13:
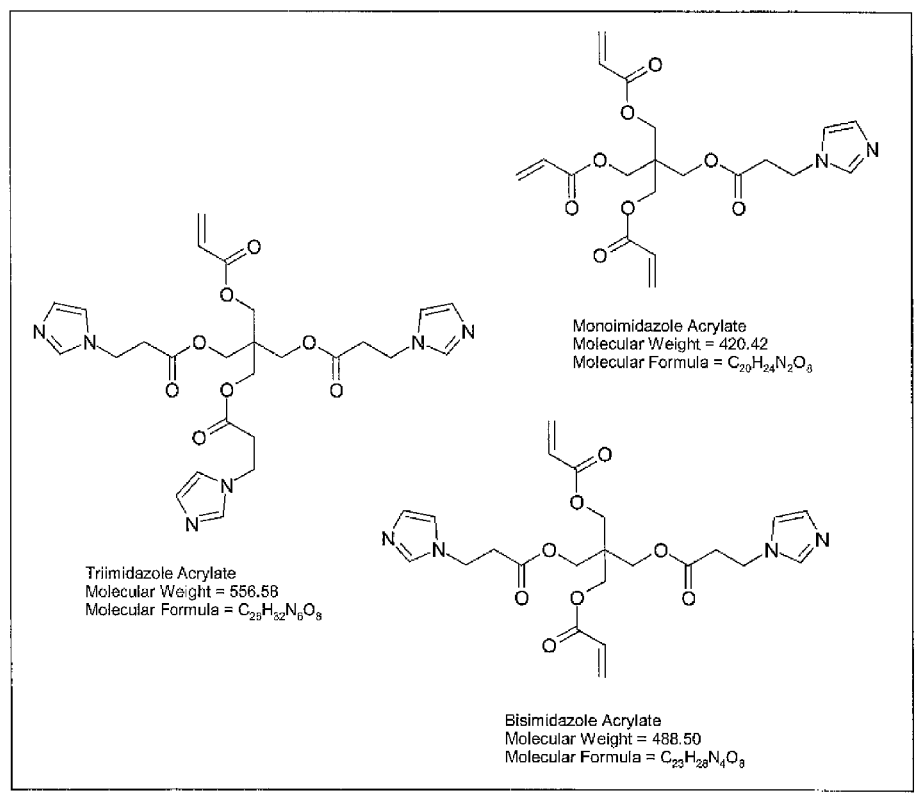
FIG. 13 depicts further examples of imidazole acrylate resins.
Figure 14:
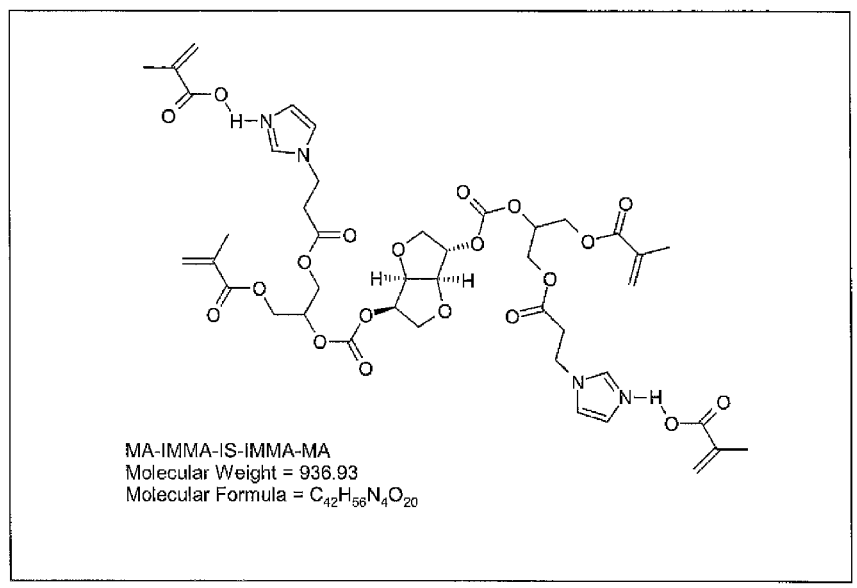
FIG. 14 depicts a complex of methacrylic acid and bisimidazole dimethacrylate resin.
Figure 15:
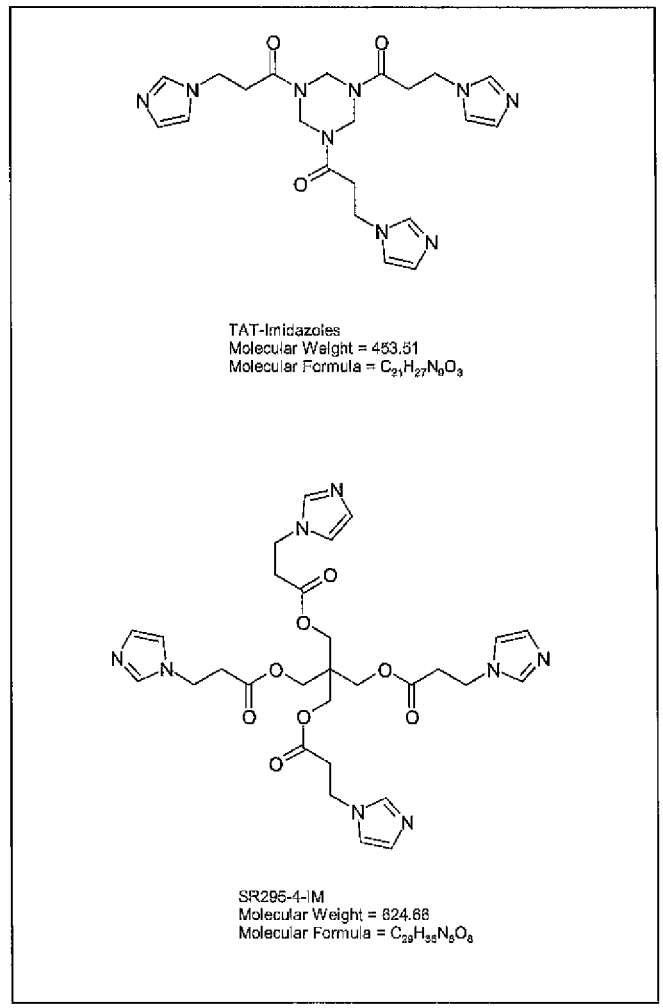
FIG. 15 depicts two typical nonpolymerizable triimidazole resin and tetraimidazole resin.
Figure 16:
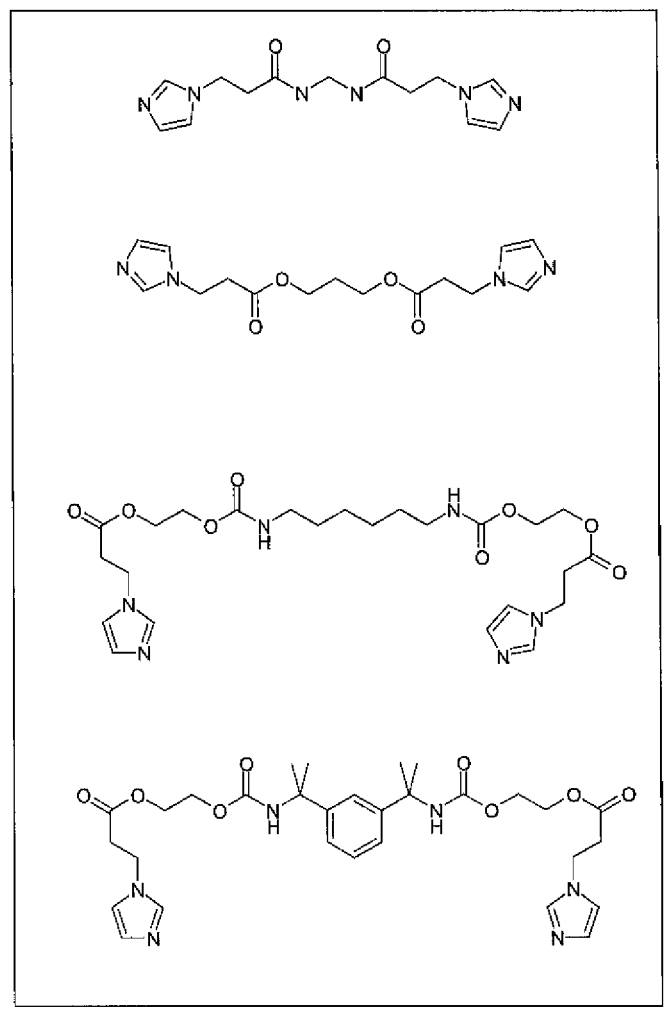
FIG. 16 depicts further nonpolymerizable bisimidazole resins.

IEM-based monoimidazole-monomethacrylate Resins (FIG. 11) was prepared via a two-step process as described in the following: to a 500 ml 3-nech round flask, 237 grams of AMAHP and 146.2 grams of 2-isocynate ethoxylmethacrylate (IEM), and 0.53 gam of DBTOL were charged at 35° C. Keep reaction for 6 hrs. 339 grams liquid resin was collected. Then 185.1 grams of the precursor resin and 800 ml of methylene dichloride were charged into a 1000 ml three neck round flask at room temperature. Then slowly it was added of 55.5 grams of imidazole crystalline powder. Keep reaction for overnight. The resulting solution was extracted several times by using aqueous solution of potassium carbonate. Then it was dried over night with magnesium sulphate prior to remove the solvent via Rotovapor at 35-40° C. under vacuum. 214 grams of liquid resin was collected.

TABLE 1

Compositions for Various Bisimidazole Dimethacrylate Resins

|  | Example 3 | Example 1 | Example 2 |
| --- | --- | --- | --- |
| Resin Composition | AMAHP/HEMA | Isosorbide/AMAHP/ TEGDMA | TCDC/AMAHP/ TEGDMA |
| IMMA Resin, | 100 | 90 | 90 |
| TEGDMA, (wt/wt, %) | 0 | 10 | 10 |
| Resin Form | Liquid | Liquid | liquid |
| Viscosity @ 20° C. Pa · s | 3 | 690 | 40 |
| Solubility @ 37° C. in water | partially soluble | partially soluble | partially soluble |
| Solubility @ 37° C. in water/ethanol(50:50, w/w %) | soluble | soluble | soluble |

TABLE 2

Physical Property for Various Imidazole-based Resin Complexes

|  | Example 1 Complex A 50% Example 1/TEGDMA(80/20) 50% OEMA/TEGDMA(75/25) | Example 1 Complex B 50% Example 1/TEGDMA(80/20) 50% PENTA/TEGDMA(75/25) | Example 1 Complex C 33% Example 1 67% PAA(50K, 25% in Water) |
| --- | --- | --- | --- |
| As-aged 2 d RT Viscosity@20° C. Pa · s | 23 | 85 | N/A |
| As-aged 2 wks RT Viscosity@20° C. Pa · s | 20 | 1610 | elastic gel |

TABLE 3

Physical Property for Various Formulated Imidazole Resins

|  | Formulated Imidazole Resin 1 80% Example 1 20% TEGDMA 0.165% CQ 0.30% EDAB 0.015% BHT | Formulated Imidazole Resin 2 100% Example 3 0.165% CQ 0.30% EDAB 0.015% BHT | Formulated Imidazole Resin 3 100% BIDMA Resin 3 0.165% CQ 0.30% EDAB 0.015% BHT |
| --- | --- | --- | --- |
| Viscosity@20° C. Pa · s | 12 | 10 | 60 |
| Shrinkage @ 24 hrs % | NA | NA | NA |
| Stress @ 60 min MPa | 1.10 | 2.30 | 0.45/0.30 |

TABLE 3-continued

Physical Property for Various Formulated Imidazole Resins

|  | Formulated Imidazole Resin 1<br>80% Example 1<br>20% TEGDMA<br>0.165% CQ<br>0.30% EDAB<br>0.015% BHT | Formulated Imidazole Resin 2<br>100% Example 3<br>0.165% CQ<br>0.30% EDAB<br>0.015% BHT | Formulated Imidazole Resin 3<br>100% BIDMA Resin 3<br>0.165% CQ<br>0.30% EDAB<br>0.015% BHT |
|---|---|---|---|
| $\Delta H_1$ in $N_2$ @ UV-Vis J/g | 119 | 107 | 83 |
| $t_o$ seconds | 14 | 17 | 28 |
| $t_{max}$ seconds | 42 | 40 | 58 |
| $\Delta H_1$ in $N_2$ @ Vis J/g | 121 | 103 | 83 |
| $t_o$ seconds | 15 | 16 | 30 |
| $t_{max}$ seconds | 45 | 38 | 77 |

TABLE 4

Physical Property for Various Formulated Imidazole Resins

|  | Formulated Imidazole Resin 4<br>80% Example 1<br>20% TEGDMA<br>0.165% CQ<br>0.30% EDAB<br>0.015% BHT | Formulated Imidazole Resin 5<br>80% Example 1<br>20% BIDMA Resin 4<br>0.165% CQ<br>0.30% EDAB<br>0.015% BHT | Formulated Imidazole Resin 6<br>80% Example 1<br>20% HEMASA<br>0.165% CQ<br>0.30% EDAB<br>0.015% BHT | Formulated Imidazole Resin 7<br>67% Example 1<br>13% MA Acid<br>20% TEGDMA<br>0.13% CQ<br>0.012% BHT<br>0.32% LTPO |
|---|---|---|---|---|
| Viscosity@20° C. Pa·s | 15 | 160 | 280 | 12 |
| Shrinkage @ 24 hrs % | NA | NA | NA | NA |
| Stress @ 60 min MPa | 1.70/1.00 | 1.15/0.50 | 0.45/0.32 | 3.50/2.40 |
| $\Delta H_1$ in $N_2$ @ UV-Vis J/g | 108 | 86 | 89 | 136 |
| $t_o$ seconds | 20 | 23 | 22 | 9 |
| $t_{max}$ seconds | 48 | 47 | 50 | 28 |
| $\Delta H_1$ in $N_2$ @ Vis J/g | 101 | 81 | 79 | 131 |
| $t_o$ seconds | 21 | 24 | 25 | 8 |
| $t_{max}$ seconds | 53 | 48 | 66 | 29 |

TABLE 5

Physical Property for Various Formulated Imidazole Composites

|  | Composite 1 | Composite 2 | Composite 3 | Composite 4 |
|---|---|---|---|---|
| Resins | 19.42%<br>IMMA Resin<br>67% Example 1<br>13% MA Acid<br>20% TEGDMA<br>0.13% CQ<br>0.012% BHT<br>0.32% LTPO | 21.05%<br>IMMA Resin<br>80% Example 1<br>20% TEGDMA<br>0.165% CQ<br>0.30% EDAB<br>0.015% BHT | 20%<br>Conventional<br>100%<br>EsthetXflow<br>Resin<br>0.10% CQ<br>1.30% EDAB<br>0.005% BHT | 20%<br>Conventional<br>100%<br>EsthetXflow<br>Resin<br>0.10% CQ<br>1.30% EDAB<br>0.005% BHT<br>1.2% Uvinol M-40<br>0.196% Flublau conc. |
| Fillers (wt/wt) | 80.58% | 78.95% | (80.0%) | 80.0% |
| Stickiness@37° C. mm | NA | NA | 0.60 | 1.30 |

TABLE 5-continued

Physical Property for Various Formulated Imidazole Composites

|  | Composite 1 | Composite 2 | Composite 3 | Composite 4 |
|---|---|---|---|---|
| Stress @ 60 min MPa |  | 2.30/1.92 | 1.81/2.58 |  |
| $\Delta H_1$ in $N_2$ @ UV-Vis J/g | 29 | 25 | 25 |  |
| $t_o$ seconds | 2 | 9 | 36 |  |
| $t_{max}$ seconds | 23 | 46 | 117 |  |
| $\Delta H_1$ in $N_2$ @ Vis J/g | 26 | 24 | 22 |  |
| $t_o$ seconds | 4 | 14 | 21 |  |
| $t_{max}$ seconds | 28 | 47 | 107 |  |

Figure 9:
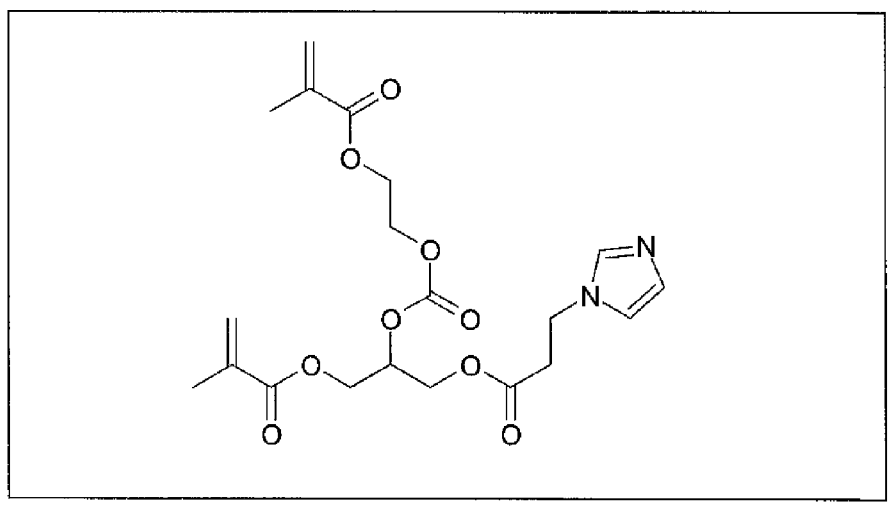
FIG. 9 depicts a HEMA based dimethacrylate imidazole resin.

One of typical acid-neutralizing polymerizable resins is polymerizable imidazole resin (Example 3) as shown in FIG. 9, which structurally is a dimethacrylate resin containing imidazole moiety. Imidazole is well known for its rather basic property; in fact it is appoxmately sixty times more basic than pyridine. Thus it should indicate that imidazole intrinsically capable to neutralize readily most of acidic compounds. In addition, unlike other organic basic compounds, such as tertiary amine, imidazole is stable towards oxidants and would not involve in any redox/H-abstraction reactions that occurred in self-cure and/or light-cure process.

There has been a compatibility issue between a simplified adhesive and a typical BPO/amine based resin cement in self-cure mode. It is believed that acid-base reaction between acid monomer in a simplified adhesive and amine in cement causes deactivation of amine as co-initiator. It was thought that a cement incorporating Resin Example 3 could neutralize acids in a simplified adhesive to mitigate or eliminate the issue of deactivation of amine in the cement. As a result, the incompatibility of a simplified adhesive and resin cement in self-cure mode may be reduced or eliminated.

TABLE 6

Base Resin Blend-1 with Imidazole-based Monomer

|  | % By Wt. |
|---|---|
| Nupol | 20.000 |
| Example 3 | 65.980 |
| TEGDMA | 10.000 |
| Camphorquinone (CQ) | 0.150 |
| EDAB | 0.160 |
| DHEPT | 1.700 |
| Uvinul M40 | 2.000 |
| BHT | 0.010 |
| Total | 100.000 |

TABLE 7

Catalyst Resin Blend-2 with Imidazole-based Monomer

|  | % By Wt. |
|---|---|
| Nupol | 20.000 |
| Example 3 | 67.700 |
| TEGDMA | 10.000 |
| Benzoyl Peroxide (BPO) | 2.200 |
| BHT | 0.100 |
| Total | 100.000 |

TABLE 8

Base Paste-1 with Imidazole-based Monomer

|  | % By Wt. |
|---|---|
| Blend-1 | 32.600 |
| Filler | 67.400 |
| Total (paste) | 100.000 |

TABLE 9

Catalyst Paste-2 with Imidazole-based Monomer

|  | % By Wt. |
|---|---|
| Blend-2 | 38.000 |
| Filler | 62.000 |
| Total | 100.000 |

When the catalyst Paste-2 was stored at RT for 72 hrs, a chuck of solid mass was seen on the bottom, most possibly due to some premature polymerization. It is assumed that some impurities in Resin Example 3 may act as self-cure co-initiators.

Comparative data results of the experimental cement and the control of Calibra are presented on Table 5 and 6. In summary, the experimental cement is compatible with Prime&Bond NT without the use of Self-cure Activator (SCA). The bond strength on dentin for Prime&Bond NT to bond the experimental cement in self-cure on dentin is similar to Prime&Bond NT in combination with a Self-cure Activator, whereas without a self-cure activator, Prime&Bond NT essentially does not bond Calibre in self-cure on dentin. The overall mechanical performance of experimental cement is similar to that of Calibra, except for somewhat lower flexural modulus.

TABLE 10

24 hr SBS of Prime&Bond NT to Bond cements in Self-cure on Dentin

| | Bonding Agent | | | |
|---|---|---|---|---|
| | Prime&Bond NT | Prime&Bond NT/SCA (1:1) | Prime&Bond NT | Prime&Bond NT |
| Cement | Calibra base/ catalyst (1:1) | Calibra base/catalyst (1:1) | Paste-1/ Paste-2 (1:1) | Paste-1/ Calibra catalyst (1:1) |
| SBS (MPa) | 1.9 (2.2) | 14.1 (2.7) | 12.0 (2.5) | 16.2 (3.4) |

TABLE 11

Mechanical Properties
Paste-1/Calibra Catalyst vs. Calibra base/catalyst in SC

| | Paste-1/Calibra catalyst | Calibra base/catalyst |
|---|---|---|
| CS (MPa) | 274 (11) | 278 (8) |
| FS (MPa) | 98 (9) | 103 (14) |
| FM (MPa) | 6173 (643) | 7086 (297) |

TABLE 12

Base Resin Blend-3 Containing DMEMA

| | % By Wt. |
|---|---|
| Nupol | 62.330 |
| DMEMA | 23.650 |
| TEGDMA | 10.000 |
| Camphorquinone (CQ) | 0.150 |
| EDAB | 0.160 |
| DHEPT | 1.700 |
| Uvinul M40 | 2.000 |
| BHT | 0.010 |
| Total | 100.000 |

*DMEMA = 2-(Dimethylamino)ethyl methacrylate

TABLE 13

Base Paste Paste-3 with DMEMA

| | % By Wt. |
|---|---|
| Blend-3 | 32.600 |
| Filler | 67.400 |
| Total (paste) | 100.000 |

When Paste-3 was mixed with Calibra catalyst paste (1:1), no curing into solid was observed even after 3 hrs.

TABLE 14

Base Resin Blend-4 with 4-VPy

| | % By Wt. |
|---|---|
| Nupol | 69.080 |
| 4-Vpy | 15.820 |
| TEGDMA | 11.080 |
| Camphorquinone (CQ) | 0.150 |
| EDAB | 0.160 |
| DHEPT | 1.700 |
| Uvinul M40 | 2.000 |
| BHT | 0.010 |
| Total | 100.000 |

*4-Vpy = 4-Vinylpyridine

TABLE 15

Base Paste-4 with 4-VPy

| | % By Wt. |
|---|---|
| Blend-4 | 32.600 |
| Filler | 67.400 |
| Total (paste) | 100.000 |

TABLE 16

Base Resin Blend-5 with MEMA

| | % By Wt. |
|---|---|
| Nupol | 56.880 |
| MEMA | 29.980 |
| TEGDMA | 9.120 |
| Camphorquinone (CQ) | 0.150 |
| EDAB | 0.160 |
| DHEPT | 1.700 |
| Uvinul M40 | 2.000 |
| BHT | 0.010 |
| Total | 100.000 |

*MEMA = 2-N-Morpholinoethyl methacrylate

TABLE 17

Base Paste Paste-5 with MEMA

| | % By Wt. |
|---|---|
| Blend-5 | 32.600 |
| Filler | 67.400 |
| Total (paste) | 100.000 |

TABLE 18

24 hr SBS of Prime&Bond NT to Bond Cements in Self-cure on Dentin

| | Bonding Agent | | | |
|---|---|---|---|---|
| | Prime&Bond NT | Prime&Bond NT/ SCA (1:1) | Prime&Bond NT | Prime&Bond NT |
| Cement | Calibra base/ catalyst (1:1) | Calibra base/ catalyst (1:1) | Paste-4/ Calibra Catalyst (1:1) | Paste-5/ Calibra Catalyst (1:1) |
| SBS (MPa) | 1.9 (2.2) | 14.1 (2.7) | 10.8 (3.4) | 6.1 (2.2) |

What is claimed are:

1. A dental composition comprising
   a. 0.5-10% wt/wt of non-polymerizable acid-neutralizing resin (I) or 0.5-99% wt/wt of an acid-neutralizing polymerizable resin (II) or a mixture of (I) and (II), featuring a moiety that is capable to effectively neutralizing an acid group, where the neutralized acid group is as carboxylic acid, sulphonic acid, phosphonic acid or phosphoric acid,
   b. 5-90% wt/wt of mixed conventional polymerizable resins;
   c. 0.01-5.00% of Initiators and other additives;
   d. 0-90% wt/wt a plurality of filler particles ranged from 10 nm-50 micron; wherein the non-polymerizable acid-neutralizing resin has a formula of (I):

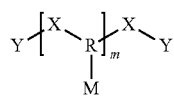
(I)

wherein the acid-neutralizing polymerizable resin has a formula (II) of:

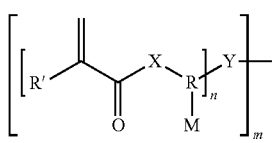
(II)

R': H or Me;
X is O, S, NH, NR1, where R1 is $CH_3$ or $C_2H_5$,
Y is O, S, NH or NR or R;
R and Y are the same or different and have $C_1$-$C_{24}$, linear and/or branched alkylene residue, or aromatic/substituted residue;
M is an alpha-substituted tertiary amine, pyridine or substituted pyridine, imidazole and/or substituted imidazole, pyrrole and/or substituted pyrrole, piperidine and/or substituted piperidine, pyrazole and/or substituted pyrazole, oxazole and/or substituted oxazole, thiazole and/or substituted thiozole, isoxazole and/or substituted isoxazole, isothiazole and/or substituted isoxazole, thiadizole indole and/or substituted thiadizole indole, indolizine and/or substituted indolizine, triazole and/or substituted triazole, tetrazole and/or substituted tetrazole, pentazole and/or substituted pentazole, quinoline and/or substituted quinoline, isoquinoline and/or substituted isoquinoline isoquinoline, pyridazine and/or substituted pyridazine, pyrimidine and/or substituted, pyzazine and/or substituted pyzazine, cinnoline and/or substituted cinnoline, phthalzine pyrimidine and/or substituted phthalzine, quinazoline and/or substituted quinazoline, quinoxaline and/or substituted quinoxaline, phenazine and/or substituted triazines, triazines and/or substituted triazines or any combination of these, and n is from 1 to 10 and m is from 1 to 10.

2. The dental composition of claim 1, wherein M is

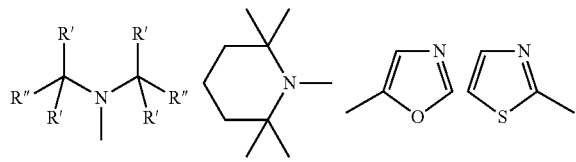

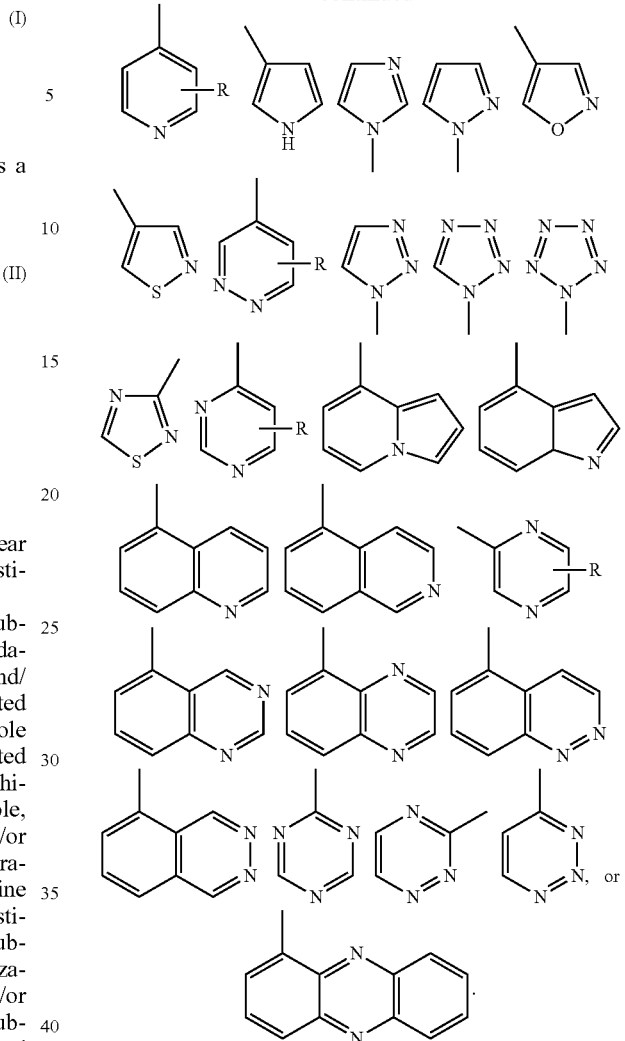

3. The dental composition of claim 1, wherein the formulated composition is capable of eliminating the need of a self-cure activator in a dental adhesive.

4. The dental composition of claim 1, wherein the formulated composition has antibacterial capability.

5. The dental composition of claim 4, wherein the formulated composition optionally includes a cationic complex with a weak acid, from which an acid exchange occurs during contact between a cured adhesive containing a strong acidic component and a dual-cure restorative containing the cationic complex.

* * * * *